(12) United States Patent
Morton et al.

(10) Patent No.: US 10,751,284 B1
(45) Date of Patent: Aug. 25, 2020

(54) TARGETED THERAPY TO DEPLETE TUMOR-ASSOCIATED MACROPHAGES (TAMS)

(71) Applicant: Verily Life Sciences LLC, Mountain View, CA (US)

(72) Inventors: Stephen Morton, Mountain View, CA (US); Graziella Solinas, Mountain View, CA (US)

(73) Assignee: VERILY LIFE SCIENCES LLC, Mountain View, CA (US)

( * ) Notice: Subject to any disclaimer, the term of this patent is extended or adjusted under 35 U.S.C. 154(b) by 0 days.

(21) Appl. No.: 15/677,555

(22) Filed: Aug. 15, 2017

Related U.S. Application Data

(60) Provisional application No. 62/377,069, filed on Aug. 19, 2016.

(51) Int. Cl.
| | |
|---|---|
| *A61K 31/4995* | (2006.01) |
| *C07K 16/40* | (2006.01) |
| *A61K 9/127* | (2006.01) |
| *C07K 16/28* | (2006.01) |
| *A61K 39/00* | (2006.01) |

(52) U.S. Cl.
CPC ........ *A61K 9/1271* (2013.01); *A61K 31/4995* (2013.01); *C07K 16/2896* (2013.01); *C07K 16/40* (2013.01); *A61K 2039/505* (2013.01)

(58) Field of Classification Search
CPC .............. A61K 9/1271; A61K 31/4995; C07K 16/2896; C07K 16/40
USPC ........................................................ 435/325
See application file for complete search history.

(56) References Cited

U.S. PATENT DOCUMENTS

| | | | | |
|---|---|---|---|---|
| 2008/0286198 | A1* | 11/2008 | Goetsch ............. | A61K 47/6805 424/1.49 |
| 2009/0175873 | A1 | 7/2009 | Liu | |
| 2012/0058177 | A1 | 3/2012 | Reisfeld et al. | |
| 2012/0258107 | A1 | 10/2012 | Graversen et al. | |
| 2012/0276193 | A1* | 11/2012 | Graversen .......... | C07K 16/2896 424/450 |

OTHER PUBLICATIONS

Allavena et al. (Clinical and Experimental Immunology, 2012, 167: 195-205).*
Sharma et al. (Journal of Drug Targeting, 2006, 14(5): 301-310).*
Akbarzadeh et al., "Liposome: classification, preparation, and applications", Nanoscale research letters 8.1 (2013): 102.
Ashley et al., "Liposomal bortezomib nanoparticles via boronic ester prodrug formulation for improved therapeutic efficacy in vivo", Journal of medicinal chemistry 57.12 (2014): 5282-5292.
Bozzuto et al., "Liposomes as nanomedical devices", International journal of nanomedicine 10 (2015): 975.
Daniel et al., "Dual-responsive nanoparticles release cargo upon exposure to matrix metalloproteinase and reactive oxygen species", Chemical Communications 52.10 (2016): 2126-2128.
Dasgupta et al., "Non inflammatory boronate based glucose-responsive insulin delivery systems", PLoS one 7.1 (2012): e29585.
De Belder et al., "Preparation and properties of fluorescein-labelled hyaluronate", Carbohydrate Research 44.2 (1975): 251-257.
De Palma et al., "Macrophage regulation of tumor responses to anticancer therapies", Cancer cell 23.3 (2013): 277-286.
Etzerodt et al., "CD163 and inflammation: biological, diagnostic, and therapeutic aspects", Antioxidants & redox signaling 18.17 (2013): 2352-2363.
Liu et al., "Legumain protease-activated TAT-liposome cargo for targeting tumours and their microenvironment", Nature communications 5 (2014): 4280.
Moon et al., "Interbilayer-crosslinked multilamellar vesicles as synthetic vaccines for potent humoral and cellular immune responses", Nature materials 10.3 (2011): 243-251.
Olympus , ""Improving Drug Delivery with Macrophage Targeting"", May 16, 2013.
Saravolac et al., "Effect of liposome-encapsulation on immunomodulating and antiviral activities of interferon-γ", Antiviral research 29.2-3 (1996): 199-207.
Zhang et al., "Biocompatible Reactive Oxygen Species (ROS)-Responsive Nanoparticles as Superior Drug Delivery Vehicles", Advanced healthcare materials 4.1 (2015): 69-76.
Non-Final Office Action for U.S. Appl. No. 15/677,559, dated Mar. 14, 2019, 14 pages.
Duluc et al., "Interferon-Gamma Reverses the Immunosuppressive and Protumoral Properties and Prevents the Generation of Human Tumor-Associated Macrophages", International Journal of Cancer, vol. 12, No. 2, 2009, pp. 367-373.
Etzerodt et al., "Efficient Intracellular Drug-Targeting of Macrophages Using Stealth Liposomes Directed to the Hemoglobin Scavenger Receptor CD163", Journal of Controlled Release, vol. 160, No. 1, May 30, 2012, pp. 72-80.
Fraternale et al., "Polarization and Repolarization of Macrophages", Journal of Clinical & Cellular Immunology, vol. 6, No. 2, Apr. 15, 2015, pp. 1-10.
Weagel et al., "Macrophage Polarization and Its Role in Cancer", Journal of Clinical & Cellular Immunology, vol. 6, No. 4, Jul. 7, 2015, pp. 1-8.
Non-Final Office Action for U.S. Appl. No. 15/677,559, dated Sep. 4, 2019, 15 pages.

(Continued)

*Primary Examiner* — Yan Xiao
(74) *Attorney, Agent, or Firm* — Kilpatrick Townsend & Stockton LLP

(57) ABSTRACT

Provided herein are tumor associated macrophage (TAM)-targeting liposome having a lipid bilayer; a targeting agent associated with the lipid bilayer, wherein the targeting agent comprises an antibody or fragment thereof that selectively binds a tumor associated macrophage; and a cytotoxic agent associated with the lipid bilayer, wherein the cytotoxic agent depletes tumor associated macrophages at or near the site of a tumor. Also provided are pharmaceutical compositions comprising the TAM-targeting liposomes and methods of treating a subject with cancer with the compositions.

11 Claims, 2 Drawing Sheets

(56) References Cited

OTHER PUBLICATIONS

Graversen et al., "Drug Trafficking Into Macrophages via the Endocytotic Receptor CD163", Membranes, vol. 5, No. 2, 2015, pp. 228-252.

Hofkens et al., "Liposomal Targeting of Prednisolone Phosphate to Synovial Lining Macrophages During Experimental Arthritis Inhibits M1 Activation But Does Not Favor M2 Differentiation", PLOS One, vol. 8, Issue 2, Feb. 2013, 11 pages.

Kono et al., "Antitumor Effect of Nuclear Factor-κB Decoy Transfer by Mannose-Modified Bubble Lipoplex Into Macrophages in Mouse Malignant Ascites", Cancer Science, vol. 105, No. 8, Aug. 2014, pp. 1049-1055.

U.S. Appl. No. 15/677,559, "Final Office Action", dated Feb. 4, 2020, 24 pages.

Cagdas et al., "Liposomes as Potential Drug Carrier Systems for Drug Delivery", Application of Nanotechnology in Drug Delivery, 2014, pp. 1-50.

Huang et al., "Targeted delivery of oligonucleotides into tumor-associated macrophages for cancer immunotherapy", Journal of Controlled Release, vol. 158, No. 2, 2012, pp. 286-292.

Kelly et al., "Targeted Liposomal Drug Delivery to Monocytes and Macrophages", Journal of Drug Delivery, vol. 2011, 2011, pp. 1-11.

Marques-Gallego et al., "Ligation Strategies for Targeting Liposomal Nanocarriers", BioMed Research International, vol. 2014, 2014, pp. 1-12.

Perche et al., "Recent Trends in Multifunctional Liposomal Nanocarriers for Enhanced Tumor Targeting", Journal of Drug Delivery, 2013, pp. 1-32.

Sercombe et al., "Advances and Challenges of Liposome Assisted Drug Delivery", Frontiers in Pharmacology, vol. 6, No. 286, 2015, pp. 1-13.

Tang et al., "Anti-tumour strategies aiming to target tumour-associated macrophages", British Society of Immunology, vol. 138, No. 2, 2012, pp. 93-104.

\* cited by examiner

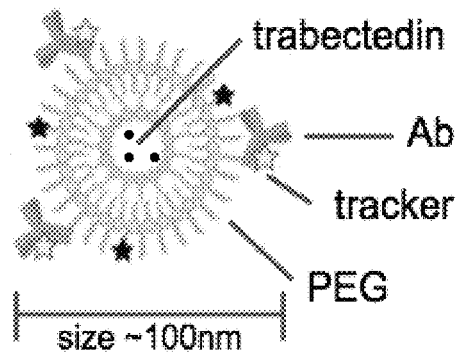
FIG. 1
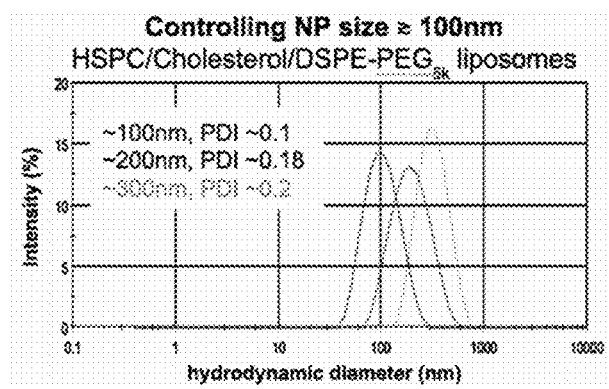 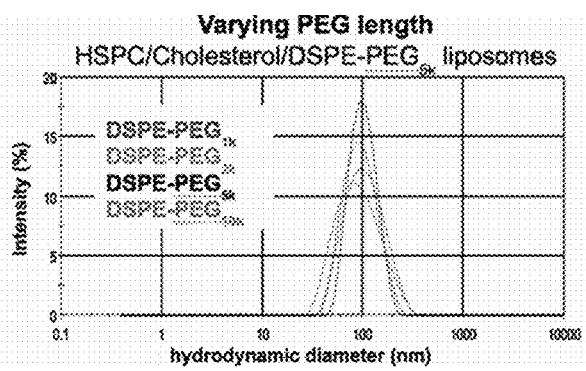
FIG. 2A          FIG. 2B

TARGETED THERAPY TO DEPLETE TUMOR-ASSOCIATED MACROPHAGES (TAMS)

CROSS REFERENCE TO RELATED APPLICATIONS

This application claims priority to U.S. Provisional Application No. 62/377,069, filed Aug. 19, 2016, which is incorporated by reference herein in its entirety.

BACKGROUND

Therapeutic agents in nanoparticles, such as liposomes, may passively reach target organs, tissues, cell, or microenvironments such as tumor microenvironments. Tumor-associated macrophages (TAMs) play a role in tumor growth and metastasis, actively maintaining a immune-suppressive state in the tumor microenvironment. TAMs also appear to contribute to resistance to various therapeutic agents and to promote tumor cell growth and metastasis.

SUMMARY

Provided herein is a TAM-targeting liposome. The liposome has a lipid bilayer; a targeting agent associated with the lipid bilayer and a cytotoxic agent associated with the lipid bilayer. The targeting agent comprises an antibody or fragment thereof that selectively binds a TAM, whereas the cytotoxic agent depletes TAMs at or near the site of a tumor. Also provided is a pharmaceutical composition comprising TAM-targeting liposomes and a method of treating a subject with cancer with the compositions or liposomes described herein.

BRIEF DESCRIPTION OF THE DRAWINGS

FIG. 1 is a schematic showing an exemplary TAM-targeted liposome. The liposome includes a lipid bilayer, a cytotoxic agent (e.g., trabectedin) and a targeting agent (e.g., an antibody (Ab)). The targeting agent associated with the surface of the liposome specifically targets TAMs. The liposome as shown includes polyethylene glycol (PEG) and a tracker (i.e., a detectable marker).

FIG. 2A is a graph showing the size distribution of liposomes made from hydrogenated soy phosphatidylcholine (HSPC), Cholesterol, and PEGylated distearoyl glycerol phosphoethanolamine (DSPE-PEG5K) and their Polydispersity Index (PDI). FIG. 2B is a graph showing the effect of varying PEG length on size distribution of HSPC:Cholesterol:DSPE-PEG liposomes at a desired size range of 100 nm.

FIG. 3A shows the results of surface incorporation of Fab using dibenzocyclooctyne (DBCO)-azide click chemistry. FIG. 3B shows the results of surface incorporation of Fab using tetrazine-trans-cyclooctene (Tz-TCO) click chemistry.

DETAILED DESCRIPTION

Figure 3A:
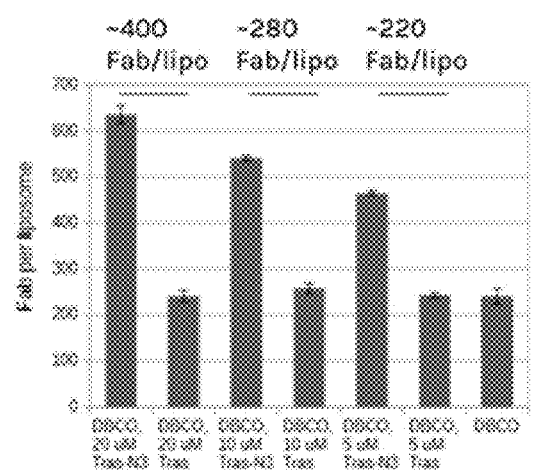
FIGS. 3A and 3B are graphs showing the number of antibody fragments (Fab) per liposome.

Tumor-associated macrophages include a variety of cell types. Activation of a macrophage typically gives rise to an M1-like phenotype, which is generally pro-inflammatory. Some TAMS, however, have an M2-like phenotype, which is associated with anti-inflammatory properties, as well as growth and tissue repair. TAMS may express a mixed M1/M2 phenotype but are usually predominately one phenotype or the other. As used herein, the term M2-like TAM refers to a TAM that predominantly exhibits the M2-like phenotype, and the term M1-like TAM refers to a TAM that predominantly exhibits an M1-like phenotype. The phenotype of a TAM or population of TAMs may be determined by a skilled artisan. For instance, an M1-like phenotype is determined by measuring increased expression of pro-inflammatory cytokines, e.g., interleukin (IL)-1β, IL-12, and tumor necrosis factor-α (TNF-α); increased production of reactive oxygen species; or antigen presentation through major histocompatibility complex (MHC) class II molecules. See, e.g., De Palma et al., Cancer Cell, 23:277-286 (2013), which is incorporated herein by reference in its entirety. An M2-like phenotype is determined by measuring increased production of anti-inflammatory cytokines, e.g. IL-10; reduced expression of pro-inflammatory cytokines; increased expression of scavenger receptors, e.g. mannose receptor (MRC1/CD206), and hemoglobin/aptoglobin scavenger receptor (CD163). See, e.g., De Palma et al., Cancer Cell, 23:277-286 (2013), which is incorporated herein by reference in its entirety.

Active targeting of liposomes to TAMs using a targeting moiety reduces degradation of the therapeutic agents contained in or attached to the liposomes and reduces the toxicity burden on the non-target parts of the body, thereby maximizing therapeutic effectiveness within the tumor microenvironment. Markers overexpressed on TAMs can be exploited to direct liposomes to the tumor and, more specifically, to the TAMs. Since all tumors are supported by TAMs, TAM-targeted liposomes provide a therapeutic approach for a broad range of cancer types. Thus, provided herein are liposomes that specifically target and deplete TAMs. The TAM-targeting liposomes include a lipid bilayer, a targeting agent associated with the lipid bilayer, and a cytotoxic agent associated with the lipid bilayer. The targeting agent optionally comprises an antibody or fragment thereof that selectively binds a TAM. The cytotoxic agent associated with the lipid bilayer optionally depletes TAMs, e.g., M2-like TAMs, at or near the site of a tumor.

As used herein, the term associated with refers to components that interact with (e.g., non-covalently), attach to (e.g., through a covalent linkage) or are otherwise located in proximity to each other. For example, an agent that is associated with a lipid bilayer may be associated with that lipid bilayer in any number of ways. The agent may be encapsulated within the lipid bilayer, directly or indirectly attached to an inner surface of the lipid bilayer, directly or indirectly (e.g., by a linker molecule(s)) attached to an outer surface of the lipid bilayer, partially or fully embedded within the lipid bilayer, or any combination thereof.

Liposomes are vesicles comprising one or more bilayers composed of amphipathic molecules, like lipids. When lipids are placed in an aqueous medium, the hydrophilic interaction of the lipid head groups results in the formation of multilamellar or unilamellar vesicles that resemble biological membranes in the form of a spherical shell. Liposomes may be small (0.025-0.05 μm) to large (0.05-10 μm). Optionally, the liposomes described herein have diameters of about 50-5,000 nm or 50-1,000 nm or diameters of less than 5,000 nm or 1,000 nm. Liposomes can be unilamellar (having one lipid bilayer) or multilamellar (having two or more lipid bilayers), and a population of liposomes may contain both unilamellar and multilamellar liposomes. See, e.g., Akbarzadeh et al., Nanoscale Res. Letters, 8:102-110 (2013), which is incorporated by reference herein in its entirety. Multilamellar liposomes as described herein optionally include cross-linkages between the lipid bilayers. Such cross linkages include, by way of example, boronic ester or thioketal crosslinkages.

As used herein, an inner cavity is the space inside the innermost a lipid bilayer of a liposome and an interbilayer or interlamellar space is the region between any two lipid bilayers. In a multilamellar liposome having, for example, three lipid bilayers, the inner cavity or core would be the space within the first (inner-most) lipid bilayer, an interbilayer space would be between the first and second (middle) lipid bilayers, and another interbilayer space would be between the second and third (outer-most) lipid bilayers.

Each bilayer of the liposome has two layers of amphipathic lipids. The hydrophobic portions of the lipids of the layers project toward each other, minimizing their interaction with the surrounding aqueous environments. The hydrophilic portions of the lipids face the opposite way and form an interface with the aqueous environment. Lipids used to prepare liposomal lipid bilayers include, but are not limited to, phospholipids, sphingolipids, glycosphingolipids, saturated glycerides, steroids such as cholesterol, synthetic phospholipids, and any combinations thereof. Optionally, one or more lipids in the lipid bilayer contains a hydroxyl group and/or a diol head group. Optionally the hydrocarbon chains of the lipids in the lipid bilayer are the same or approximately the same length. The lipids of the lipid bilayer can include one or more different types of lipids. Optionally, the lipids comprise hydrogenated soy phosphatidylcholine (HSPC), distearoyl glycerol phosphoethanolamine (DSPE), or a combination thereof. The two or more lipids may be packed together to form a bilayer or certain of the lipids may be integrated into the hydrophobic portion of the bilayer. It should be noted that a lipid bilayer may be continuous or composed of islands of lipid bilayer. It should also be understood that the hydrocarbon chains of any of various lipids can be of the same or differing lengths. Optionally one or more of the lipids are PEGylated.

Although liposomal lipid bilayers typically contain lipids as the predominant structural molecule, the bilayers or the lipids themselves may contain one or more additional components. Optionally, the additional components include, but are not limited to, detergents, protein-conjugated molecules, PEGylated molecules, and molecules with aliphatic anchors. The additional components may be inserted into lipid bilayers by, for instance, hydrophobic interaction, non-covalent attachment to lipid bilayers, or covalent attachment to lipid bilayers by, for instance, bond formation with lipid head groups. The additional components in the liposomal lipid bilayers may alter the properties of the lipid bilayer, including but not limited to, membrane fluidity, permeability, flexibility, fusogenicity, stability, charge/electrostatics, symmetry, cellular uptake, degradation, and the like. By way of example, addition of cholesterol to a lipid bilayer decreases permeability and fluidity of the liposome, whereas PEG increases the duration of circulation. See e.g., Bozzuto et al., *Intl J. of Nanomedicine,* 10: 975-999 (2015), which is incorporated herein by reference in its entirety.

Methods for making liposomes are known. For example, liposomes may be prepared by dissolving lipids in a solvent, which may optionally contain an emulsifier, followed by drying to form a thin lipid film. The lipid film is then hydrated to form sheets of lipid bilayers. Using hydration and agitation or sonication, for example, the lipid bilayers form spherical lipid bilayers. Fusion, extrusion, solvent addition, freeze-thaw, detergent removal, or further agitation may be used, as desired, to control liposome homogeneity in size and lamellarity. For instance, extrusion and sonication can produce unilamellar liposomal vesicles. A liposome including one or more targeting molecules and therapeutic agents (e.g., a cytotoxic agent) agents can be made by a variety of methods. See, e.g., Bozzuto et al., *Intl J. of Nanomedicine,* 10: 975-999 (2015); Akbarzadeh et al., *Nanoscale Res. Letters,* 8:102-110 (2013), which are incorporated herein by reference in their entireties.

The provided liposomes include one or more targeting agents associated with a lipid bilayer, optionally on the outer surface of the lipid bilayer of the liposome. In multilamellar liposomes, the one or more targeting agents or moieties are optionally associated with at least the outermost lipid bilayer and optionally on the outer surface of the outermost lipid bilayer. The targeting agent optionally comprises an antibody or fragment thereof that selectively binds a TAM, but other targeting agents (e.g., a receptor ligand or portion thereof) may be used so long as they selectively bind a TAM. Optionally, the targeting agent binds a TAM-specific marker selected from the group consisting of a scavenger receptor, a chemokine receptor, a cytokine receptor, a toll-like receptor, a NOD-like receptor, a RIG-I-like receptor, a C-type lectin receptor, a pattern recognition receptor, an enzyme, or any combination thereof. Optionally, the liposome includes one or more targeting agents selectively bind CD163 or legumain. Optionally, the liposome includes a targeting agent that binds CD163 and a targeting agent that binds legumain.

The targeting moiety may be associated with the liposome in one or more ways. It may be directly attached to the lipids of the lipid bilayer, for example, by attachment to a lipid head group. Optionally, the targeting agent is attached to a second component that is part of or associated with the lipid bilayer. The second component can be a lipid, a linker, PEG or other molecule in the lipid bilayer. Thus, by way of example, the targeting moiety can be attached to PEG, which is associated with the lipid bilayer. The targeting agent is optionally embedded within the lipid bilayer, attached to an outer surface of the lipid bilayer, or a combination thereof.

As used herein, embedded refers to the insertion of a hydrophobic portion of a molecule into the hydrophobic region of a lipid bilayer such that the inserted molecule is stabilized in the membrane at least partially by hydrophobic interactions. A fully embedded molecule refers to a molecule in which the entire structure of the molecule is embedded within the hydrophobic region of a lipid bilayer. A partially embedded molecule refers to a molecule in which a portion of the molecule is embedded within the hydrophobic region of a lipid bilayer and a portion of the molecule is either embedded in the hydrophilic region of a lipid bilayer (e.g. in the lipid head groups) or protrudes from either surface of the lipid bilayer. By way of example, a targeting moiety comprising an antibody or fragment thereof attached to a second component or directly to a lipid in the lipid bilayer is a partially embedded molecule containing a portion embedded within the hydrophobic region of the lipid bilayer and a portion that protrudes from the surface of the lipid bilayer (the antibody or fragment thereof).

The provided liposomes also include one or more cytotoxic agents associated with the lipid bilayer, wherein the cytotoxic agent depletes tumor associated macrophages at or near the site of a tumor. As used herein, deplete means to kill, induce cell death (e.g., apoptosis), render non-viable, or otherwise neutralize the function of a cell. Thus, the cytotoxic agents are, optionally, anti-tumor or anti-cancer agents. Optionally, the cytotoxic agent reduces the number of TAMs (e.g., M2-like TAMs) at or near the site of a tumor. Suitable cytotoxic agents, include, but are not limited to, alkylating agents, anti-metabolite, mitotic inhibitor, or any combination thereof. Optionally, the cytotoxic agent is trabectedin.

The cytotoxic agent may be associated with the liposome in one or more ways. The cytotoxic agent may be encapsulated within the core of the lipid bilayer, attached to an inner surface of the lipid bilayer, attached to an outer surface of the lipid bilayer, embedded within the lipid bilayer, or any combination thereof. A cytotoxic agent encapsulated within the lipid bilayer may be located in the inner cavity or within the interbilayer spaces of the liposomes. A cytotoxic agent attached to an inner or outer surface of the lipid bilayer directly (e.g., covalent attachment to a lipid) or indirectly (e.g., by attachment to a component associated with the lipid bilayer, e.g., PEG).

FIG. 1 depicts an exemplary structural arrangement of a liposome comprising a lipid bilayer, a targeting agent, and a cytotoxic agent. As shown in FIG. 1, the lipid bilayer surrounds an inner cavity or core containing a cytotoxic agent (trabectadin). The targeting agents (antibodies (Ab)) are associated with the lipid bilayer via PEG molecules. The antibody as shown in FIG. 1 is attached to a detectable marker (tracker). Additional detectable markers can be attached to the lipids or PEG molecules, as shown.

The liposomes described herein can include one or more additional active agents. Suitable additional active agents include, but are not limited to, nucleic acids, polypeptide, antibodies, small molecules, lipids, carbohydrates, and any combination thereof. The additional active agent or agents may be a therapeutic agent (e.g., a chemotherapeutic agent or phototherapeutic agent), a diagnostic or tracking agent (e.g., a detectable marker), or any combination thereof. The additional active agent or combination of active agents may be associated with the liposome in one or more ways, including the same associations that the cytotoxic agent may have with the liposome.

Detectable marker is meant any detectable label or tag that can be attached directly (e.g., a fluorescent molecule integrated into a polypeptide, such as an antibody or other targeting agent or a lipid) or indirectly (e.g., by way of a spacer, a molecule such as PEG) It should be noted that detection may involve additional steps, such as use of a secondary or tertiary antibody or ligand which is itself labeled but which binds selectively to the targeting agent, for example. A detectable marker may be visualized with a variety imaging methods. The detectable marker can be a radio-opaque substance, a radiolabel, a fluorescent label, or a magnetic label. The detectable marker is optionally selected from the group consisting of gamma-emitters, beta-emitters, and alpha-emitters, positron-emitters, X-ray-emitters and fluorescence emitters suitable for localization. Suitable fluorescent compounds include fluorescein sodium, fluorescein isothiocyanate, phycoerythrin, and TEXAS RED® sulfonyl chloride (Molecular Probes, Eugene, Oreg.). See, e.g., de Belder and Wik (Preparation and properties of fluorescein-labelled hyaluronate. Carbohydr. Res. 44(2):251-57 (1975). One skilled in the art is able to ascertain how to attached a detectable label and how to visualize a detectable label.

The herein described liposomes may release the associated cytotoxic agent and one or more additional active agents at or near the site of a tumor or tumor microenvironment. Optionally, the cytotoxic agent is released from the liposome in the presence of TAMs selectively bound by the targeting agent. Thus, release of the cytotoxic agent may be initiated upon binding of the targeting agent(s) to the TAMs. Such stimulated release of the cytotoxic agent aids in preventing and/or reducing the cytotoxic agent's systemic effects. Optionally, release of the cytotoxic agent reduces the number of TAMs, e.g., M2-like TAMs, at or near the site of a tumor.

Additional components of the lipid bilayer or agents to be added to the inner cavity or interlamellar space(s) may be added during formation of the liposomes or added after formation of the liposomes. If, for example, cytotoxic agents or other components are added during formation of the liposome, they are added to the nascent liposomes (e.g., to the lipid solution, to the thin lipid film, to the sheet of lipid bilayer, or during hydration or sonication). If, for example, a PEG or other component is added after formation of the liposome, the PEG is added after the lipid bilayers are sealed to form stable liposomes, for example, by attachment to the surface of the liposomes.

Also described herein are pharmaceutical compositions comprising the TAM-targeting liposomes and a pharmaceutically acceptable carrier. Suitable carriers and excipients and their formulations are described in Remington: The Science and Practice of Pharmacy, 22nd Edition, Lloyd V. Allen, Jr., ed., Pharmaceutical Press (2012). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. A pharmaceutical composition generally comprises agents for buffering and preservation in storage and for appropriate delivery, depending on the route of administration.

The compositions for administration will commonly include the TAM-targeting liposomes and a pharmaceutically acceptable carrier, optionally an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Dispersions of the liposomes can also be prepared in glycerol, liquid polyethylene glycols, mixtures thereof, and in oils. Under ordinary conditions of storage and use, these preparations may contain a preservative to prevent the growth of microorganisms.

The liposomes or pharmaceutical compositions containing the liposomes may be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation.

Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the liposomes may be incorporated with excipients and used in the form of ingestible tablets, buccal tablets, troches, capsules, elixirs, suspensions, syrups, wafers, and the like. Such compositions and preparations should contain at least 0.1% of the cytotoxic agent or liposomes. The percentage of the compositions and preparations may, of course, be varied and may conveniently be between about 2 to about 75% of the weight of the unit, or preferably between 25-60%. The amount of liposomes and cytotoxic agent in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the liposomes in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of liposomes can be presented in unit-dose or multi-dose sealed containers, such as ampules and vials. Thus, the composition can be in unit dosage form. In such form, the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Compositions can be formulated to provide quick, sustained or delayed release after administration by employing procedures known in the art. Certain carriers may be more preferable depending upon, for instance, the route of administration and concentration of composition being administered. Suitable formulations for use in the provided compositions can be found in Remington: The Science and Practice of Pharmacy, 22nd Edition, Lloyd V. Allen, Jr., ed., Pharmaceutical Press (2012).

The provided compositions including the TAM-targeting liposomes are useful for treating cancer in a subject. Thus, provided is a method of treating a subject with cancer comprising administering to the subject an effective amount of the TAM-targeting liposome as described herein. Optionally, a pharmaceutical composition including the TAM-targeting liposomes and a pharmaceutically acceptable excipient is administered to the subject. In the methods of treatment, the liposomes or compositions comprising liposomes specifically bind to and deplete TAMs. Administration of the pharmaceutical composition optionally reduces the number of TAMs at or near the site of a tumor. Optionally, the targeted and depleted TAMs are M2-like tumor associated macrophages.

As used herein, the term cancer refers to all types of cancer, neoplasm, or malignant tumors found in mammals, including carcinomas, sarcomas, germ cell tumors, blastomas whether primary tumors or metastatic tumors. Exemplary cancers include cancer of the brain, breast, cervix, colon, bladder, head and neck, thyroid gland, adrenal gland, pancreas, liver, kidney, lung, ovary, testes, stomach, esophagus, genitourinary tract, prostate, and uterus. Specific examples include non-small cell lung, melanoma, mesothelioma, multiple myeloma, neuroblastoma, rhabdomyosarcoma, malignant pancreatic insulanoma, medulloblastoma, and endometrial cancer.

Compositions comprising the herein disclosed TAM-targeting liposomes may be delivered to a subject with cancer in a variety of ways, including intravenously, intramuscularly, subcutaneously, intraperitoneally, inhalation, intubation, topically, orally, local injection, or the like. If the TAM-targeting liposomes or compositions thereof are administered in more than one dose, the TAM-targeting liposomes or composition may be administered by the same or by different delivery methods for the various doses. The TAM-targeting liposomes or composition containing the liposomes may be administered locally or systemically. When the liposomes or compositions are administered systemically, the liposomes may circulate and remain intact until the targeting agent binds a TAM. When the targeting agent binds a TAM, the cytotoxic agent and, if present, additional active agents, are optionally released at or near the site of a tumor.

As used herein, the term treat refers to any delay in onset or one or more symptoms or clinical signs, reduction in the frequency or severity of symptoms, amelioration of symptoms, improvement in patient comfort or function, decrease in severity of the disease state, etc. The effect of treatment can be compared to an individual or pool of individuals not receiving a given treatment or to the same patient prior to or after cessation of treatment. Treatment includes partial or complete ablation of the disease. The term prevent refers to a decrease in the occurrence of a given disease (e.g., a primary cancer or metastasis). Prevention may be complete (no detectable symptoms) or partial, such that occurrence is delayed or results in fewer symptoms than would occur absent treatment. Prevention optionally occurs before diagnosis or after a determination of a pre-cancerous condition. Prevention optionally refers to after diagnosis where metastasis is prevented.

By effective dose or amount as used herein is meant a dose of liposomes or pharmaceutical composition containing the liposoms that produces the desired effect(s) (i.e., treating or preventing cancer). Determining the dosage and formulation is within the skill of the skilled artisan. See, e.g., Lieberman, Pharmaceutical Dosage Forms (vols. 1-3, 1992); Lloyd, The Art, Science and Technology of Pharmaceutical Compounding (1999); Remington (2012); and Pickar, Dosage Calculations ($9^{th}$ edition) (1999)). An effective dose or amount may ameliorate one or more symptoms or clinical signs of a disease. For example, for a given parameter (e.g., a clinical sign or symptom), an effective amount shows a desired increase or decrease of at least 5%, 10%, 15%, 20%, 25%, 40%, 50%, 60%, 75%, 80%, 90%, or 100%. The efficacy may also be expressed as "-fold" increase or decrease. For example, an effective amount results in at least a desired 1.2-fold, 1.5-fold, 2-fold, 5-fold increase or decrease as compared to a standard control. An effective amount may prevent or delay the onset of a disease or one or more symptoms of a disease.

The exact dose, formulation, and dosing regimen of the TAM-targeting liposomes will depend on a number of factors including the purpose of the treatment, the species of the subject, the age and weight of the subject, the disease to be treated, the severity of the disease, the amount and type of active agent in the liposomes, and the like. Determining the dosage, formulation and dosing regimen is within the skill of one skilled in the art using known techniques. See, e.g., Lieberman, Pharmaceutical Dosage Forms (vols. 1-3, 1992); Lloyd, The Art, Science and Technology of Pharmaceutical Compounding (1999); Remington (2012); and Pickar, Dosage Calculations ($9^{th}$ edition) (1999)). Thus, treatment may include administering a single dose or multiple doses of the TAM-targeting liposomes or compositions thereof. The TAM-targeting liposomes or composition containing the liposomes, as disclosed herein, can be administered to the subject, for example, daily, multiple times daily (e.g., 2, 3, 4, or 6 times daily), weekly, multiple times weekly, monthly, multiple times monthly or any effective regimen. The treatment can be administered alone or in combination with any other treatment modalities or agents. The additional treatment can be administered simultaneously with the first treatment, at a different time, or on an entirely different therapeutic schedule (e.g., the first treatment can be daily, while the additional treatment is weekly).

In the provided methods of treatment, additional therapeutic agents can be used that are suitable for treating cancer or for treating the side-effects of other therapeutic agents. Thus, the provided methods of treatment optionally further comprise administering one or more additional therapeutic agents to the subject. Suitable additional therapeutic agents include, but are not limited to, analgesics, anesthetics, analeptics, corticosteroids, anticholinergic agents, anticholinesterases, anticonvulsants, antineoplastic agents, allosteric inhibitors, anabolic steroids, psychotherapeutic agents, neural blocking agents, anti-inflammatory agents, antibiotics, antifungals, antihistamines, antimuscarinic agents, antimycobacterial agents, immunological agents, muscarinics, protease inhibitors, anti-angiogenic or vascular-disrupting agents, vitamins, growth factors, and hormones. The choice of agent and dosage can be determined readily by one of skill in the art based on the given disease being treated.

Combinations of agents or compositions can be administered either concomitantly (e.g., included in the liposomes or as a mixture of additional agents with the liposomes), separately but simultaneously (e.g., via separate intravenous lines or by different by simultaneous forms of administration) or sequentially (e.g., one agent or composition is administered first followed by administration of the second agent or composition). Thus, the term combination is used to refer to concomitant, simultaneous or sequential administration of two or more agents or compositions.

Optionally, the liposomes or compositions thereof contain a detectable marker for use in a method of diagnosis or a method of tracking the therapeutic agent in vivo. The method comprises administering the a subject an effective amount of the provided liposomes comprising a detectable marker or a composition of such liposomes and visualizing or localizing the marker at the site of the cancer. The method of localization depends on the type of detectable marker selected and includes, by way of example, x-ray, CT scan, MRI, radionuclide scanning, ultrasound, PET scanning, and the like. Furthermore, localization can include biopsy of a tissue and subsequent histological visualization (e.g., by immunohistochemistry). In each case, Also described herein are kits comprising the disclosed TAM-targeting liposomes or pharmaceutical compositions thereof. The kit comprises one or more dosage units of TAM-targeting liposomes or the pharmaceutical composition thereof. Optionally, the kit comprises instructions for use, one or more additional agents, and/or devices for administering the liposomes or composition. Delivery devices include, but are not limited to, syringes, drip bags, patches, and inhalers. The kit may comprise a solution for reconstituting or diluting the liposomes or composition of liposomes. For example, if a disclosed composition is provided in a solid form that is to be reconstituted for parenteral administration, the kit can comprise a sealed container of a suitable solution in which the disclosed composition can be dissolved to form a liposome-containing solution suitable for parenteral administration. Examples of acceptable solutions include, but are not limited to: water sodium chloride solution, Ringer's, dextrose, dextrose and sodium chloride, and lactated Ringer's.

Disclosed are materials, compositions, and components that can be used for, can be used in conjunction with, can be used in preparation for, or are products of the disclosed methods and compositions. These and other materials are disclosed herein, and it is understood that, when combinations, subsets, interactions, groups, etc. of these materials are disclosed, that, while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein are hereby specifically incorporated by reference in their entireties and at least for the material for which they are cited.

The examples below are intended to further illustrate certain aspects of the methods and compositions described herein, and are not intended to limit the scope of the claims.

EXAMPLES

Example 1. Liposome Synthesis

Liposomes were synthesized by dissolving lipids in organic solvent, drying the lipids to produce a lipid film, hydrating the lipid film, and functionalizing the liposomes by surface conjugation of targeting molecules. In one example, heat-treated scintillation vials were first prepared by storing 20 mL scintillation vials in an oven at 230° C. for at least 2 hours prior to film preparation. 12 mg 1,2-dipalmitoyl-sn-glycero-3-phosphoethanolamine (DPPE)+/− 0.3 mg were added to the vials. 4 mg cholesterol of a 10 mg/mL stock solution in 2:1 (v/v) chloroform:methanol were then added. A fluorescent dye tracker can optionally be incorporated into the liposomes by first conjugating cyanine5.5 (e.g., cyanine5.5-NHS ester; Lumiprobe) to DPPE, and adding 0.4 mg cyanine5.5-conjugated DPPE from a 1 mg/mL stock solution in 2:1 (v/v) chloroform:methanol. 0.5% DPPE-PEG-X conjugate were added, where X is methyltetrazine, azide, TCO, DBCO, or other click chemistry handle. 5 mL of 2:1 (v/v) chloroform:methanol were then added to fully dissolve all lipid components. Optionally, lipid soluble components, for instance, a lipid soluble cytotoxic agent, may be added according to methods known in the art. The lipid solution was dried down to a uniform lipid film in a rotary evaporator. The vial was sealed with perforated parafilm and placed in desiccator for at least 2 hours to remove trace volatile organics.

The lipid film was hydrated by suspension in 5 mL hydration buffer (10 mM HEPES buffer pH 7.4) while sonicating under applied heat. Trabectedin can be added to the lipid solution. Liposomes were formed by agitating the lipid suspension, for example by sonication, vortexing, or shaking. Small liposomes (e.g., 200 nm or less in diameter) may be prepared by extruding the hot mixture through filters of the desired size. Liposome suspensions were cooled to room temperature and diluted three-fold with phosphate-buffered saline (PBS). Liposomes were then concentrated to approximately 3-4 mL via spin filtration in 30 kDa MWCO filters.

Associating a targeting agent (e.g., Ab or Fab) to the TAM-targeting liposome functionalized the surface of the liposome. A click handle on the targeting agent complementary to a click chemistry present on the liposome was activated according to methods known in the art. For example, a liposome comprising 1,2-distearoyl-sn-glycero-3-phosphoethanolamine-PEG-tetrazine (DSPE-PEG-Tz) is associated with a targeting agent modified specifically or nonspecifically with the complementary trans-cyclooctene (TCO) click handle. 1 µM targeting molecule (e.g., anti-CD163 Ab or anti-legumain Ab) was added to the liposomes, and the click chemistry association was performed according to methods known in the art at room temperature for 16 hours. Unassociated antibodies were removed by passing the liposomes through a size-exclusion chromatograph (SEC) column using Sephacryl 400 resin. Where Cy5.5 tracker was used, eluted liposomal fractions containing high fluorescence were selected for further analysis.

Using this protocol, liposomes could be scalably and reproducibly manufactured with very precise control over size, composition, and surface characteristics (e.g., association of a wide range of targeting agents, including proteins and small molecules). FIG. 2A shows reproducible control over the size (e.g., diameter) of liposomes produced according to the methods described herein. FIG. 2B shows the herein described methods to produce liposomes can be used to vary the liposomal composition (e.g., variable PEG length) without significantly changing the physicochemical characteristics of the resulting liposomes.

Figure 3B:
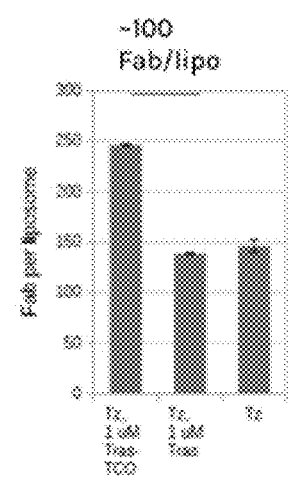

Additionally, the surface properties of TAM-targeting liposomal prepared according to this protocol could be well controlled. FIG. 3 shows the reproducible association and titration of targeting agents (e.g., Fab for HER2) on the surface of TAM-targeting liposomes using two different click chemistries for association (DBCO-azide and Tz-TCO chemistries). The number of targeting agents associated with the TAM-targeting liposomes could be varied according to the conditions for formation of the association.

Example 2. Evaluation of Tumor-Targeted Liposome Cytotoxic Activities In Vitro with Human and Mouse Primary Macrophages TAM-targeted liposomes may be evaluated for cytotoxic activities in vitro using human and/or mouse primary macrophages. Macrophages may be modulated upon liposome phagocytosis. Quantification of macrophage modulation may be performed by gene expression analysis of inflammatory and anti-inflammatory markers, measurement of inflammatory secreted factors, and/or immunofluorescence for surface markers of macrophage polarization. Cytotoxicity of liposomes may be analyzed by determining the cytotoxic activity (e.g., cytotoxic dose) of liposomes encapsulating a cytotoxic agent (e.g., trabectedin) in tumor-conditioned macrophages (TCMs) generated from tumor cell supernatants, as compared to the cytotoxicity of free, unassociated cytotoxic agent in TCMs. The specificity and cytotoxic activity of TAM-targeted liposomes on other tumor infiltrating stromal cells (T cells, B cells, fibroblasts) may also be evaluated. Additionally, the cytotoxic activity of TAM-targeted liposomes in co-culture experiments with macrophages and tumor cells may also be evaluated.

For co-culture experiments, 40 µL of human macrophages are polarized in 384-well microtiter plates. For unstimulated (M0) macrophages, 10 µL growth medium are added. For M1 polarized macrophages, LPS and IFN-γ are added to final concentrations of 1 ng/mL and 50 ng/mL, respectively, in 50 µL final volumes. For M2 polarized macrophages, dexamethasone and IL-4 were added to final concentrations of 100 nM and 20 ng/mL, respectively, in 50 final volumes. The M0, M1 and M2 Macrophages and tumor cells are co-cultured by first thawing and culturing stocks of MDA MB 231 GFP-expressing breast cancer cells (available from Cell Biolabs, Inc., San Diego, Calif.). Cells are harvested and counted on the date of the experiment. For each time point during co-culture, five cell concentrations are used. Cells are serially diluted according to the following: 1:1 (2,500 cells/µL), 1:2 (1250 cells/µL), 1:5 (625 cells/µL), 1:10 (313 cells/µL), and 1:20 (156 cells/µL). Cells are treated with TAM-targeting or control liposomes to determine the cytotoxicity activity of the TAM-targeting liposomes at each time point.

Example 3. In Vivo Characterization of TAM-Targeting Liposomes

TAM-targeting liposomes may be evaluated in vivo, for instance in rodents, canines, primates, or other mammals. Multiple mouse tumor models may be used to evaluate the anti-tumor activity, pharmacokinetics, biodistribution, and pharmacodynamics of TAM-targeting liposomes as single agents or in combination with checkpoint inhibitors. Tumor models can be selected from models having high infiltration of TAMs (e.g., fibrosarcoma, pancreatic, mammary, ovarian, etc.). Mass cytometry (CyTOF) may analyze modulation of immune cells in blood, spleen, lymph nodes and tumor upon treatment with TAM-targeting liposomes. Changes in secreted factors may be analyzed by biological detection and quantification technologies such as those available from Luminex. Histological staining of biopsied tissue samples can be used to visualize localization of TAM-targeting liposomes in tumor microenvironments and other relevant tissues. In vivo toxicity can be evaluated by a number of methods, such as by maximum tolerated dose (MTD) assays, gross toxicity, hepatic and/or renal function tests, and the like. Cross-species variation in biological performance may be evaluated by several methods, such as pharmacokinetic (PK) and/or pharmacodynamic (PD) variations in treatment outcomes, and variations in biodistribution, efficacy, and toxicity profiles.

What is claimed is:

1. A tumor associated macrophage (TAM)-targeting liposome comprising:
    a. a lipid bilayer, wherein the lipid bilayer comprises PEGylated distearoyl glycerol phosphoethanolamine (DSPE-PEG);
    b. a targeting agent associated with the lipid bilayer, wherein:
        the targeting agent comprises an antibody or fragment thereof that selectively binds a tumor associated macrophage,
        the targeting agent selectively binds a TAM-specific scavenger receptor, and
        the TAM-specific scavenger receptor is CD163; and
    c. a cytotoxic agent associated with the lipid bilayer, wherein:
        the cytotoxic agent depletes tumor associated macrophages at or near the site of a tumor, and
        the cytotoxic agent is trabectedin.

2. The TAM-targeting liposome of claim 1, wherein the targeting agent is embedded within the lipid bilayer, attached to an outer surface of the lipid bilayer, or a combination thereof.

3. The TAM-targeting liposome of claim 1, wherein the cytotoxic agent is encapsulated within the lipid bilayer, attached to an inner surface of the lipid bilayer, embedded within the lipid bilayer, or any combination thereof.

4. The TAM-targeting liposome of claim 1, wherein the cytotoxic agent is released from the liposome in the presence of tumor associated macrophages selectively bound by the targeting agent.

5. The TAM-targeting liposome of claim 1, wherein the liposome further comprises one or more additional active agents.

6. The TAM-targeting liposome of claim 1, wherein the tumor associated macrophages are M2-like tumor associated macrophages.

7. A pharmaceutical composition comprising the TAM-targeting liposome of claim 1 and a pharmaceutically acceptable carrier.

8. The TAM-targeting liposome of claim 1, wherein the cytotoxic agent is embedded within the lipid bilayer, the targeting agent is attached to an outer surface of the lipid bilayer, and the tumor associated macrophages are M2-like tumor associated macrophages.

9. The TAM-targeting liposome of claim 1, wherein the cytotoxic agent is attached to an outer surface of the lipid bilayer.

10. The TAM-targeting liposome of claim 9, wherein the TAM-targeting liposome has a diameter of 200 nm or less.

11. The TAM-targeting liposome of claim 10, wherein the lipid bilayer further comprises hydrogenated soy phosphatidylcholine (HSPC) and cholesterol.

* * * * *